US012607630B2

(12) United States Patent
Alava et al.

(10) Patent No.: US 12,607,630 B2
(45) Date of Patent: Apr. 21, 2026

(54) BIOLOGICAL AND/OR BIOCHEMICAL AND/OR CHEMICAL SENSOR

(71) Applicants: COMMISSARIAT A L'ENERGIE ATOMIQUE ET AUX ENERGIES ALTERNATIVES, Paris (FR); UNIVERSITE GRENOBLE ALPES, Saint-Martin-d'Heres (FR); CENTRE NATIONAL DE LA RECHERCHE SCIENTIFIQUE, Paris (FR)

(72) Inventors: Thomas Alava, Grenoble (FR); Pascal Mailley, Grenoble (FR); Yanxia Hou-Broutin, Bilieu (FR); Loic Leroy, Grenoble (FR)

(73) Assignees: 1) COMMISSARIAT A L'ENERGIE ATOMIQUE ET AUX ENERGIES ALTERNATIVES, Paris (FR); UNIVERSITE GRENOBLE ALPES, Saint-Martin-d'Heres (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 735 days.

(21) Appl. No.: 17/999,728

(22) PCT Filed: May 26, 2021

(86) PCT No.: PCT/FR2021/050951
§ 371 (c)(1),
(2) Date: Nov. 23, 2022

(87) PCT Pub. No.: WO2021/240110
PCT Pub. Date: Dec. 2, 2021

(65) Prior Publication Data
US 2023/0236182 A1 Jul. 27, 2023

(30) Foreign Application Priority Data
May 27, 2020 (FR) ...................................... 2005584

(51) Int. Cl.
*G01N 33/543* (2006.01)
*G01N 21/552* (2014.01)
(Continued)

(52) U.S. Cl.
CPC ..... *G01N 33/54373* (2013.01); *G01N 21/553* (2013.01); *G01N 33/56911* (2013.01);
(Continued)

(58) Field of Classification Search
None
See application file for complete search history.

(56) References Cited

U.S. PATENT DOCUMENTS

2016/0011216 A1   1/2016   Feller et al.
2017/0227556 A1   8/2017   Feller et al.
(Continued)

OTHER PUBLICATIONS

International Search Report issued Sep. 10, 2021 in PCT/FR2021/050951, filed on May 26, 2021, 3 pages.
(Continued)

*Primary Examiner* — Rebecca M Giere
(74) *Attorney, Agent, or Firm* — Oblon, McClelland, Maier & Neustadt, L.L.P.

(57) ABSTRACT

A sensor may include a prism having a first face; a metal first layer covering, via a contact face, the first face; a light source; and a matrix-array detector; the device may include a dielectric second layer on which rests a transistor including a sheet made of a two-dimensional material, intended to form a channel region, a front face of the sheet comprising a specific functionalization via which specific targets are liable to be adsorbed, the specific functionalization being suitable for placing the adsorbed specific targets at a smaller distance Dd below which detection via electrical measurement by means of the specific transistor and via measurement of resonance of surface plasmons is possible.

20 Claims, 5 Drawing Sheets

(51) Int. Cl.
 *G01N 33/569* (2006.01)
 *G01N 33/94* (2006.01)
(52) U.S. Cl.
 CPC ..... *G01N 33/946* (2013.01); *G01N 2333/245*
 (2013.01); *G01N 2333/974* (2013.01)

(56) References Cited

U.S. PATENT DOCUMENTS

| | | |
|---|---|---|
| 2018/0217138 A1 | 8/2018 | Han et al. |
| 2019/0257843 A1 | 8/2019 | Feller et al. |
| 2019/0257844 A1 | 8/2019 | Feller et al. |

OTHER PUBLICATIONS

Smith et al., "Wavelength-selective visible-light detector based on integrated graphene transistor and surface plasmon coupler", Proc. of SPIE vol. 9083, 7 pages.

Taylor et al., "Quantitative and simultaneous detection of four foodborne bacterial pathogens with a multi-channel SPR sensor", Biosensors and Bioelectronics 22 (2006), pp. 752-758.

Su et al., "Two-dimensional nanomaterials for biosensing applications", Trends in Analytical Chemistry 119, 2019, 14 pages.

Stojanovic et al., "Aptamer-Based Folding Fluorescent Sensor for Cocaine", J. Am. Chem. Soc. 2001, 123, pp. 4928-4931.

Paborsky et al., "The Single-stranded DNA Aptamer-binding Site of Human Thrombin", The Journal of Biological Chemistry, vol. 268, No. 28, 1993, pp. 20808-20811.

Wang et al,. "Label-free, regenerative and sensitive surface plasmon resonance and electrochemical aptasensors based on graphene", Chem Commun, vol. 47, 2011, pp. 7794-7796.

Maurya et al., "Improved performance of the surface plasmon resonance biosensor based on graphene or MoS2 using silicon", Optics Communications 359, 2018, pp. 426-434.

Melaine et al., Gold Nanoparticles Surface Plasmon Resonance Enhanced Signal for the Detection of Small Molecules on Split-Aptamer Microarrays (Small Molecules Detection from Split-Aptamers), Microarrays 2015, 12 pages.

Melaine et al., "A nanoparticle-based thermo-dynamic aptasensor for small molecule detection", Nanoscale 8, 2016, 8 pages.

BIOLOGICAL AND/OR BIOCHEMICAL AND/OR CHEMICAL SENSOR

CROSS-REFERENCE TO RELATED APPLICATIONS

The present application is the national stage of international application PCT/FR2021/050951, filed on May 26, 2021, and claims the benefit of the filing date of French Appl. No. 2005584, filed on May 27, 2020.

TECHNICAL FIELD

The present invention relates to the field of sensors, and more particularly to biological and/or biochemical and/or chemical sensors. In particular, the present invention relates to a sensor using surface plasmon resonance and the characterisation of the electrical properties of transistors suitable for the detection of biological and/or biochemical and/or chemical species.

PRIOR ART

FIG. 1 shows a surface plasmon resonance imaging sensor 1 known from the prior art. This device 1 comprises in particular:

- a prism 2 which comprises a face, referred to as the first face 2$a$;
- a metal layer 3 covering with one of its faces, referred to as the contact face 3$a$, the first face 2$a$;
- a light source 4 intended to emit light radiation at an angle of incidence $\theta i$ on the contact face 3$a$;
- a detector 5, for example a CCD or CMOS detector, intended to collect the light radiation emitted by the light source and reflected by the contact face 3$a$.

In operation, the light source 4 emits light radiation in the direction of the contact face 3$a$ at a varying angle of incidence $\theta i$, for example in a continuous manner over a range of angles. This light radiation is then reflected by the contact face 3$a$ to be collected by the detector 5.

However, there is an angle of incidence $\theta p$ for which the energy carried by the incident light radiation creates an evanescent wave OV (shown in FIG. 1) which is likely to enter into resonance with an electromagnetic wave of surface plasmons of the metal layer 3. This phenomenon results in a decrease in intensity of the reflected light radiation detected at the detector 5 as illustrated in FIG. 2.

In FIG. 2, a sharp drop in the relative intensity of the reflected light radiation can be clearly seen for an angle of incidence $\theta i$ greater than 54°, and which reaches its minimum for the angle of incidence $\theta p$, otherwise referred to as the plasmon resonance angle. The latter depends on the wavelength of the light radiation, but also on the optical index of the dielectric medium in contact with the exposed face 3$b$ of the metal layer 3 and opposite the contact face 3$a$.

The angle of incidence $\theta p$, in FIG. 2, depends however on the optical properties of the materials used and the characteristics, and in particular the wavelength, of the light source.

It has been shown that this type of sensor, which makes it possible to detect extremely small variations in the optical index of the dielectric medium, can advantageously be used for the detection of biological and/or biochemical and/or chemical species (referred to in the following as "target").

Indeed, the simple adsorption of targets on the exposed face 3$b$ of the metal layer 3 modifies locally the optical index of the interface formed by the metal layer 3 and the dielectric medium. The variation in index which results in a variation in the plasmon resonance angle is thus a parameter of choice for the detection and/or identification of targets.

In order to make the analysis of targets selective, the functionalisation of the exposed face 3$b$ may be considered. This functionalisation makes it possible in particular to make the adsorption at the exposed face 3$b$ selective at a given type of target, referred to as the specific target. In other words, the functionalisation of the exposed face has the sole purpose of limiting the adsorption phenomenon to the specific target. This functionalisation generally involves chemical or biochemical or biological species (referred to in the following as "probes") grafted onto the exposed face 3$b$. For example, the probes can comprise an aptamer at which a target formed by adenosine may be adsorbed.

Thus, the implementation of functionalisation by means of a specific probe makes such a surface plasmon resonance sensor specific to a given target, referred to as a specific target. In particular, this specific sensor can be used for the detection of the specific target contained in a liquid wetting the exposed face 3$b$. This detection can be carried out up to a distance of at least 100 nm from the exposed face 3$b$.

Nevertheless, the adsorption selectivity is not perfect, such that interference phenomena are likely to occur. These are due in particular to the adsorption, via a non-specific interaction, of non-specific targets present in the fluid during analysis. This interference phenomenon degrades the quality of detection, and can, if necessary, be a source of error in the analysis of a given fluid.

For example, such a sensor can be functionalised with an aptamer acting as a specific probe interacting in a specific manner (even preferentially) with adenosine. Nevertheless, the selectivity of this interaction is not perfect, the specific probe may also interact with proteins other than adenosine. This latter interaction degrades the quality of detection and distorts the result.

Furthermore, this technique is often limited to the detection of targets with a high molar mass and/or relatively high concentration.

Alternatively, a graphene sensor, and in particular a transistor made of graphene, may be used for detecting the specific target in a liquid. This type of sensor, which also involves a functionalisation similar to that of a surface plasmon resonance sensor is also sensitive to interference phenomena related to the presence of non-specific targets (in other words, other than the specific target).

Furthermore, such a transistor, although relatively efficient for the detection of targets of low molar mass and/or low concentration, remains limited to the detection of the latter within a several tens of nanometres of the surface of said transistor.

Furthermore, the extreme sensitivity of graphene to its environment limits the field of application to the analysis of low complex solutions.

Thus, an aim of the present invention is to propose a sensor for the detection and recognition of biological, and/or biochemical and/or chemical species with improved efficiency.

Another aim of the present invention is to propose a sensor for the detection and recognition of targets with improved sensitivity.

DISCLOSURE OF THE INVENTION

The aims of the invention are, at least in part, achieved by a biological and/or biochemical and/or chemical sensor comprising:

a prism which comprises a face, referred to as the first face;

a first metal layer covering a face, referred to as the contact face, of the first face;

a light source intended to emit light radiation at an angle of incidence θi on the contact face;

a detector intended to collect the light radiation emitted by the light source and reflected by the contact face;

the device comprises a second layer of dielectric material covering the first layer, and on which a transistor rests, said transistor comprises a sheet, made of a two-dimensional material, intended to form a channel region and resting with a rear face on the second layer, a front face of the sheet, opposite its rear face, comprises a functionalisation with specific probes at which specific targets of a target family are capable of being adsorbed, the specific functionalisation being adapted to place the specific adsorbed targets at a distance lower than a detection distance Dd, below which the combined detection by electrical measurement by means of the transistor and by surface plasmon resonance measurement is possible.

According to one embodiment, the functionalisation is also adapted to keep any target other than the specific target that may be adsorbed at specific probes at a distance greater than the detection distance Dd, so that only the detection of said targets by surface plasmon resonance is possible.

According to one embodiment, the specific probes are biological or biochemical or chemical agents grafted onto the front face, each specific probe being adapted so that when the specific target is adsorbed at the specific probe, said probe deforms so as to place said specific target at a distance from the front face lower than that of the detection distance Dd.

According to one embodiment, the sensor comprises at least one reference transistor, which comprises a reference sheet, made of two-dimensional material, and the reference sheet, intended to form a channel region, rests with a rear face on the second layer, the reference sheet also comprises a reference face and is adapted to be the site of adsorption of targets in a non-selective manner, so that the latter can be detected in a combined measurement at the reference face by surface plasmon resonance initiated by the light source, and by electrical measurement by means of the reference transistor, the first layer advantageously forming a gate electrode of the at least one reference transistor.

According to one embodiment, the device comprises at least one site, at a section exposed to the external environment of the first layer, dedicated solely to measurement by surface plasmon resonance.

According to one embodiment, the two-dimensional material comprises at least one material selected from: graphene, molybdenum sulphide.

According to one embodiment, the metal material comprises at least one element selected from: gold, aluminium, copper, silver.

According to one embodiment, said device further comprises a cover covering the first face, and in which a fluid flowing from an inlet path to an outlet path of said cover, is capable of being the subject of molecular recognition by means of said device.

According to one embodiment, the light source and the detector are arranged to allow measurements to be carried out at different angles of incidence θi.

According to one embodiment, the light source is polychromatic, and is arranged with the detector so that the surface plasmon resonance measurement is performed at a fixed angle.

According to one embodiment, the detector is a matrix detector.

According to one embodiment, the specific probe is adapted to promote the adsorption of *Escherichia coli* bacteria, and the recognition of a target specific to this family.

According to one embodiment, the specific functionalisation is adapted to promote the adsorption of targets of the cocaine family.

According to one embodiment, the specific functionalisation (155) is adapted to promote the adsorption of α-thrombin.

BRIEF DESCRIPTION OF THE DRAWINGS

Further features and advantages will be given in the following description of a biological and/or biochemical and/or chemical sensor according to the invention, given as a non-limiting examples, with reference to the accompanying drawings in which.

DETAILED DESCRIPTION OF PARTICULAR EMBODIMENTS

The present invention relates to a biological and/or biochemical and/or chemical sensor, and in particular the recognition of biological and/or biochemical and/or chemical species, such as for example *Escherichia coli* bacteria.

The sensor according to the present invention comprises in particular a site, referred to as a recognition site, enabling a combined measurement to be made involving surface plasmon resonance imaging and recognition by means of a field effect transistor (referred to in the following as a "transistor").

This combined measurement on the same recognition site makes it possible in particular to better differentiate between biological and/or biochemical and/or chemical agents which can be detected by either or both of the two techniques involved.

The following description refers to the terms "probe" and "target".

The term "target" means a biological or biochemical or chemical species present in a solution, for example a liquid solution. In particular, this target, according to the present invention, is intended to be detected by a sensor described below.

The term "probe" is defined as a biological or biochemical or chemical agent grafted onto a surface so as to form a functionalisation layer on said surface. These probes can be adapted to promote the adsorption of targets on the surface in question.

Furthermore, and by definition according to the present invention, the adsorption of a given target, referred to as a specific target, at the level of given probes, referred to as specific probes, may give rise to a particular interaction. This interaction, called a specific interaction, in addition to the adsorption phenomenon, may give rise to a structural deformation of the probe. In particular, this deformation may involve the folding of the specific probe so as to bring the specific target closer to the surface. Of course, the interaction between a specific probe and any target, other than the specific target, will be limited to simple adsorption of the target in question.

Figure 1:
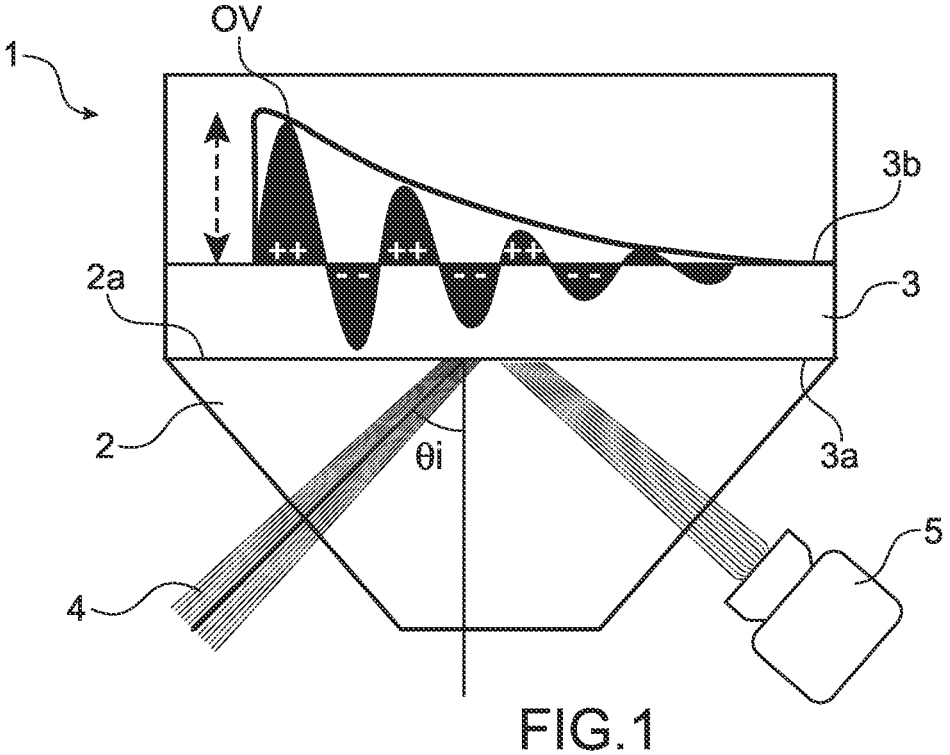
FIG. 1 is a schematic representation in a cross-sectional plane perpendicular to the first layer of a surface plasmon resonance device known from the prior art.
Figure 2:
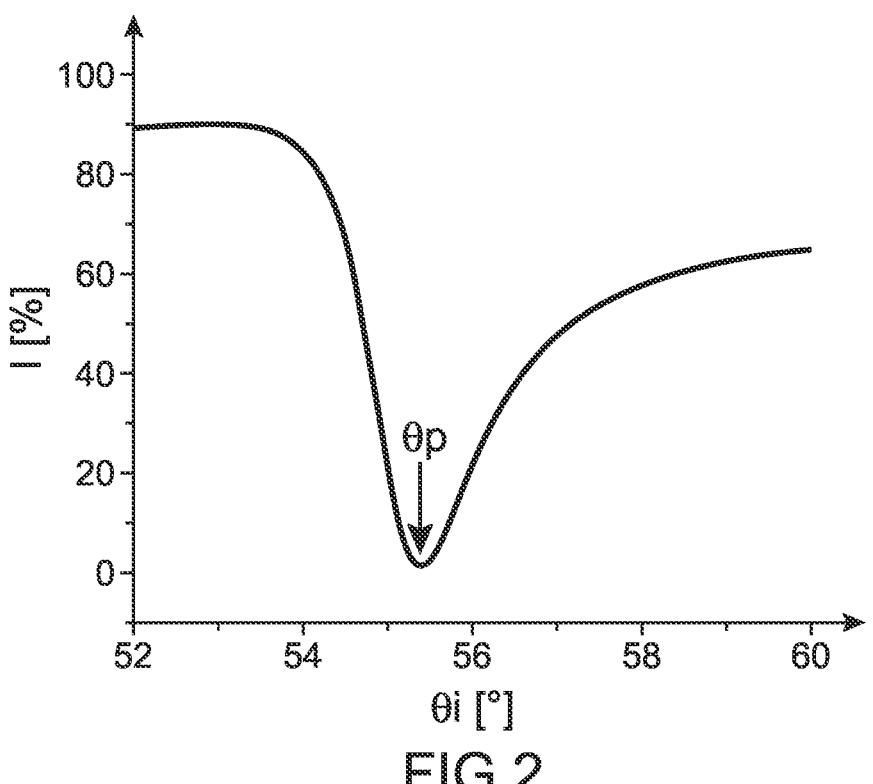
FIG. 2 is a graphical representation of the relative intensity I of reflected light radiation (vertical axis, in "%") as a function of the angle of incidence θi (horizontal axis, in " ")
Figure 3:
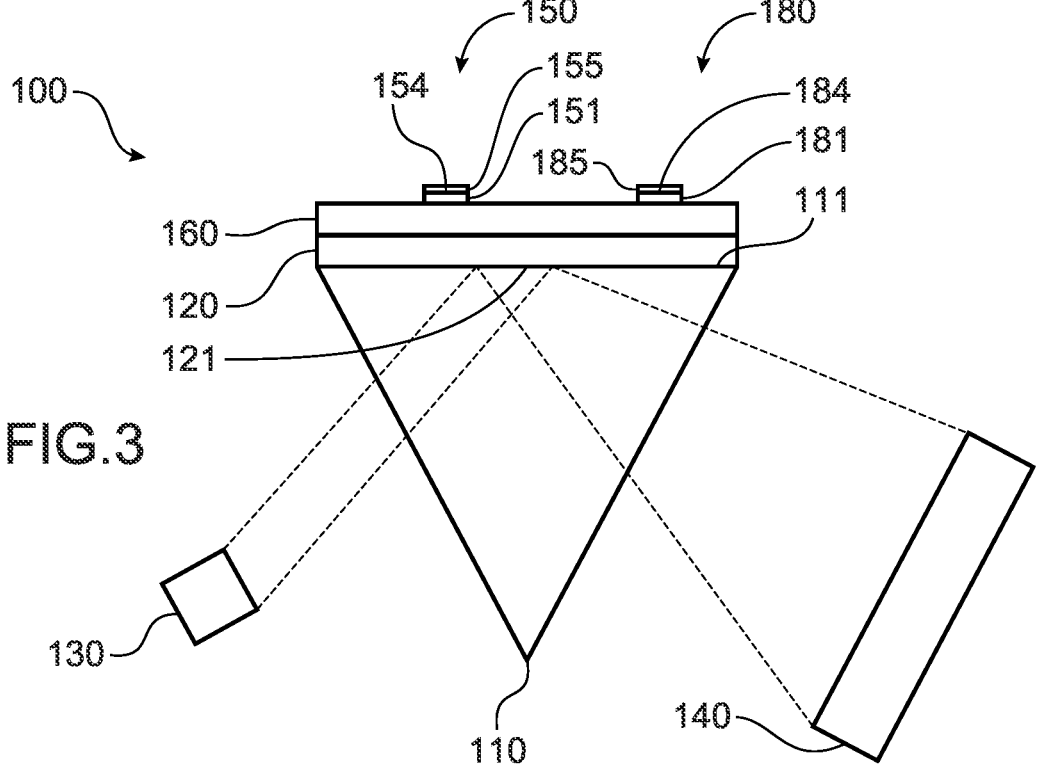
FIG. 3 is a cross-sectional representation of a sensor according to the present invention.

FIG. 3 is a schematic representation of a biological and/or biochemical and/or chemical sensor 100 (referred to in the following as "sensor 100") according to the present invention.

In particular, the sensor 100 comprises a support 110.

This support 110 is in particular transparent to the light radiation emitted by a light source 130 described in the following. This support 110 may comprise a glass plate or a prism.

The remainder of the description and the Figures refer only to the prism without limiting the invention in this respect.

The prism 110 is provided with a first face 111. The prism 110 may consist of glass in particular.

One layer, referred to as the first layer 120, rests with one of its faces, said contact face 121, on the first face 111. The first layer 120 comprises a metal material, and more particularly at least one material selected from: gold, aluminium, copper, silver.

An adhesive layer may also be interposed between the first face and the first layer 120. This first layer may comprise in particular Ni or Co, for example with a thickness between 2 nm and 3 nm.

The first layer 120 may have a thickness E of between 15 nm and 100 nm.

The sensor 100 further comprises a light source 130 intended to emit light radiation at an angle of incidence θi on the contact face 121.

More particularly and according to a first variant, the light source 130 can be arranged so that the angle of incidence θi varies, in particular continuously, in a range of angles of incidence, for example beyond the angle of total reflection. The light radiation that can be emitted by the source of light radiation is advantageously non-coherent. In this respect, the light source 130 may comprise a light-emitting diode emitting visible radiation, for example red.

According to a second variant, the light source 130 is polychromatic and emits light radiation at a fixed angle.

The sensor 100 also comprises a detector 140.

The detector 140 may comprise one or more point detectors. According to another aspect, the detector 140 may be a matrix detector.

The term "matrix detector" means a detector provided with a plurality of detection cells arranged in a grid of rows and columns. More particularly, the detection cells are arranged at the intersection of the rows and columns.

The matrix detector 140 may comprise for example a CCD or CMOS type detector.

The detector 140 is further arranged to collect the light radiation emitted by the light source 130 and reflected by the contact face 121.

6

Figures 4A, 4B, 4C:
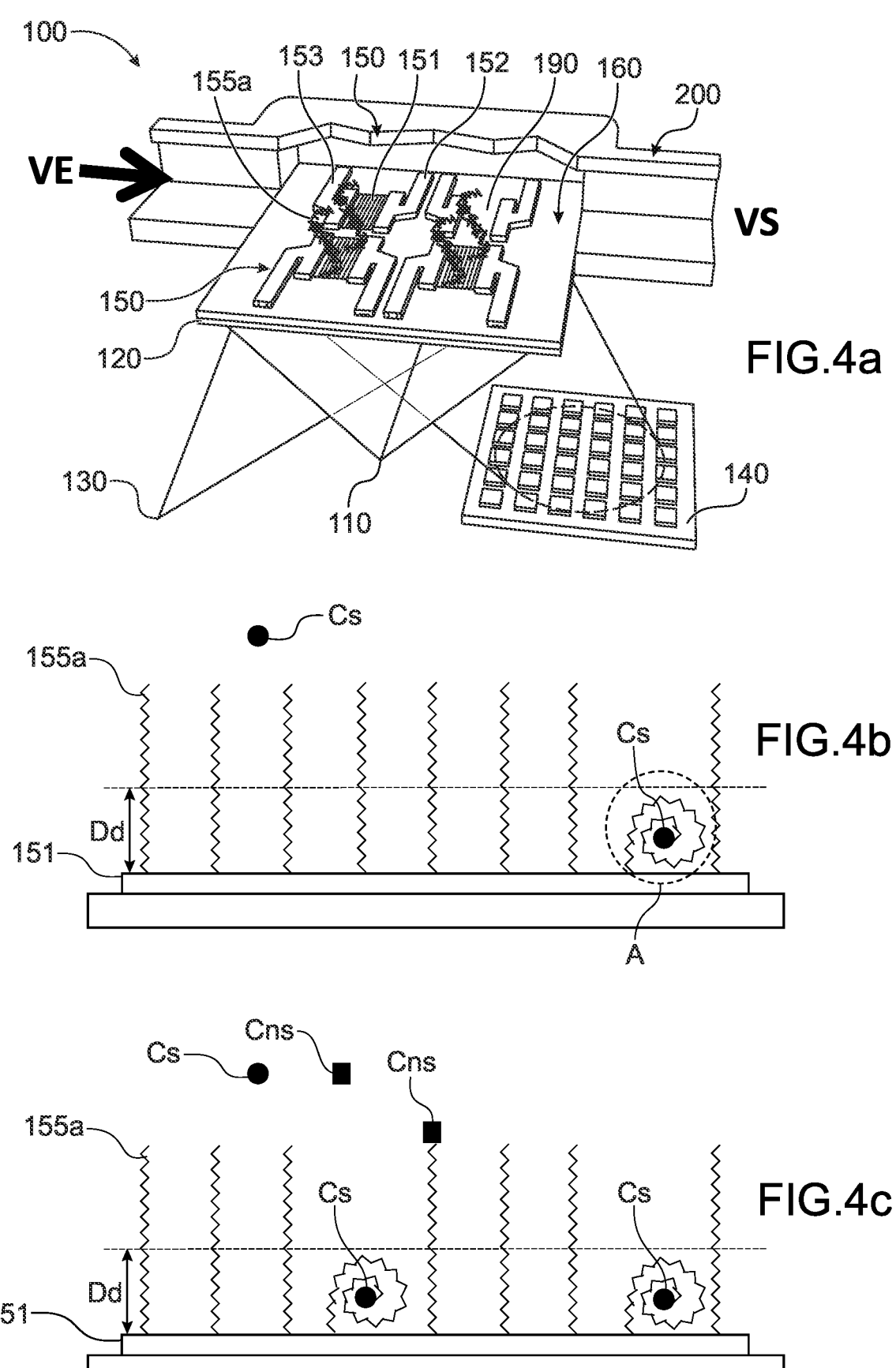
FIG. 4a is a perspective view of the biological and/or biochemical and/or chemical sensor according to the present invention.
FIG. 4b is an illustration of the adsorption mechanism via the specific interaction between a specific target and a specific probe.
FIG. 4c is an illustration of the effect of absorption of targets other than the specific targets at the specific probes.

The sensor 100 according to the present invention further comprises at least one transistor 150, and a second layer 160, made of a dielectric material interposed between the first layer 120 and at least one transistor 150 (FIGS. 3 and 4a).

The dielectric material may comprise at least one material selected from: silicon nitride, silicon oxide, hafnium oxide.

In particular, the transistor 150 comprises a sheet 151 made of a two-dimensional material, resting with its rear face on the second layer 160 and is intended to form a channel region of the transistor 150.

The term "two-dimensional material" means a material which has a 2-dimensional crystalline structure. Such materials generally comprise a stack of crystalline planes within which the atoms or molecules are linked by covalent bonds, while interactions of the Van der Walls type ensure cohesion between crystalline planes.

In an advantageous manner, the two-dimensional material is optically transparent to the light radiation likely to be emitted by the light source.

The term "optically transparent" means having a transmission coefficient greater than 70%.

Thus, the two-dimensional material may comprise at least one material selected from: graphene, molybdenum sulphide.

The transistor 150 also comprises two electrodes, referred to respectively as a source electrode 152 and drain electrode 153.

The sheet 151 also comprises a face opposite the rear face of said sheet, said front face 154, which comprises a specific functionalisation 155. This specific functionalisation 155 comprises in particular specific probes 155a at which specific targets, from a family of targets, are capable of being adsorbed (FIG. 4a).

In particular, the specific functionalisation 155 is adapted to place at a distance lower than a detection distance Dd the specific targets able to be adsorbed at the specific probes. The detection distance is in particular a distance below which combined detection is possible by electrical measurement by means of the transistor 150 and by surface plasmon resonance measurement.

FIG. 4b is an illustration of the adsorption mechanism and the specific interaction described at the beginning of this section. In particular, FIG. 4b shows the sheet 151 onto which specific probes 155a are grafted. In particular, in this FIG. 4b, the specific interaction (zone A of FIG. 4b) of a specific target Cs with one of the specific probes 155a leads to the folding onto itself of said probe so as to bring the target in question closer to a distance less than distance Dd.

Conversely, the specific functionalisation 155 can be adapted to keep at a distance greater than the detection distance Dd any target other than the specific target and which may be adsorbed at specific probes. Thus, according to this aspect, only the detection of said targets (other than the specific target) is possible by surface plasmon resonance.

FIG. 4c shows in this respect the effect of adsorption of targets other than specific targets, referred to as non-specific Cns targets. Since according to this aspect, the specific interaction does not take place between the specific probes and the non-specific Cns targets, the deformation and/or folding of said probes 155a is not observed. In this way, these non-specific targets remain at a distance from the front face, and in particular at a distance greater than the distance Dd.

In an advantageous manner, the specific probe may comprise a biological agent, and in particular an aptamer for example for the detection of adenosine.

Thus, such a sensor 100 can be used advantageously for the analysis of a complex solution comprising different targets of a specific target family.

In particular, consideration of the specific functionalisation 155 in terms of the present invention, namely a specific functionalisation 155 allowing the specific target to be located exclusively in the detection field of the transistor, allows the presence of said target, also detected by surface plasmon resonance, to be confirmed. The specific probes are further adapted to keep any target other than the specific target within the detection range of the transistor.

In other words, the sensor 100 as described, exacerbates the advantages of two probes having different detection fields, sensitivities and selectivities.

Indeed, detection by surface plasmon resonance makes it possible to detect, with a high degree of selectivity the presence of specific targets in a detection field which may extend over a hundred nanometres from the front face 154. The transistor 150 for its part is very sensitive to the presence or absence of the specific target in its detection field which may extend several tens of nanometres, in particular 20 nm, from the front face 154. In addition, keeping targets other than the specific target outside this detection field eliminates any detection of these targets other than the specific target by the transistor 150.

The device 100 according to the present invention may also comprise at least one reference transistor 180. The latter comprises in this respect a reference sheet 181, made of the two-dimensional material, and intended to form a channel region.

The reference transistor 180 also comprises two electrodes referred to respectively as the source electrode 182 and drain electrode 183.

The reference sheet 181 rests with a rear face on the second layer 160 and also comprises a reference face 174.

Said reference face is adapted to be the site of adsorption of the targets regardless of their type, so that the latter can be detected during a combined measurement, at the level of the reference face, by resonance of surface plasmons initiated by the light source, and by electrical measurement by means of the reference transistor 180.

This reference site makes it possible to know the response of the sensor 100 in the absence of functionalisation, and consequently to make differential measurements.

The sensor 100 may also comprise at least one site 190, at the level of a section exposed to the external environment of the first layer, dedicated solely to measurement by surface plasmon resonance. In particular, this site makes it possible to make reference and calibration measurements (FIG. 4a).

The sensor 100 may also be provided with a cover 200 (cross-sectional view in FIG. 4a) covering the first face, and wherein a fluid, flowing from an inlet path VE to an outlet path VS of said cover, may be subject to molecular recognition by means of said device.

The first layer 120 essentially considered for the generation of surface plasmons, may also form gate electrodes of the various transistors described in the present invention. In particular, this first layer may be structured in order to address the different transistors either individually or in groups. This last aspect makes it possible to simplify the device and in particular its manufacturing process.

The sensor 100 according to the present invention is not limited to the implementation of only one transistor per transistor type. In this respect, it may be envisaged to implement a plurality of specific transistors and references. Computer processing may then be implemented to process the data collected at the detector 140.

Furthermore, the sensor 100 according to the present invention, due to increased sensitivity and selectivity, opens the way to the detection of small size targets (and in particular with a size of less than 2 nm) and/or low concentration and/or low molar mass. It is possible according to a first example to detect traces of drugs and in particular traces of cocaine taken as a specific target. This specific target can in particular interact with a specific probe made of an MNS-4.1 type aptamer as described in document [1] cited at the end of the description.

According to a second example, the specific probe may comprise a thrombin aptamer for the detection of α-thrombin as described in document [2] cited at the end of the description.

In general, the sensor 100 may comprise a plurality of transistors each functionalised with a different specific probe. These different specific probes open the way for the analysis of complex fluids comprising different types of specific targets.

Figure 5A:
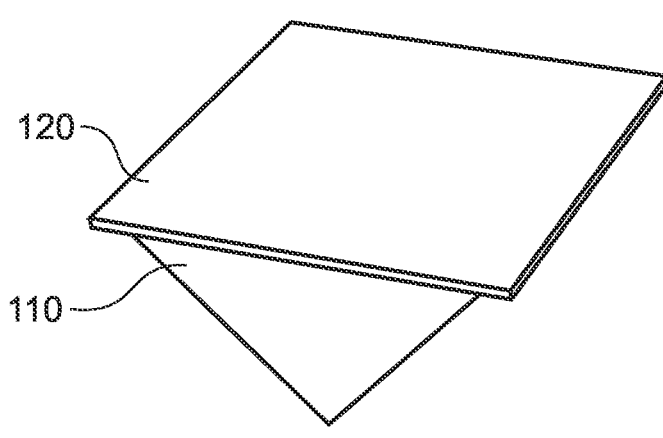
FIGS. 5a, 5b, 5c, 5d, 5e, 5f are schematic representations of different steps of manufacturing the biological and/or biochemical and/or chemical sensor according to the present invention.

The method for manufacturing such a sensor is described in relation to FIGS. 5a to 5f. In particular, FIG. 5a represents a step of forming the first layer 120, made in particular of gold, onto first face of a prism.

Figure 5B:
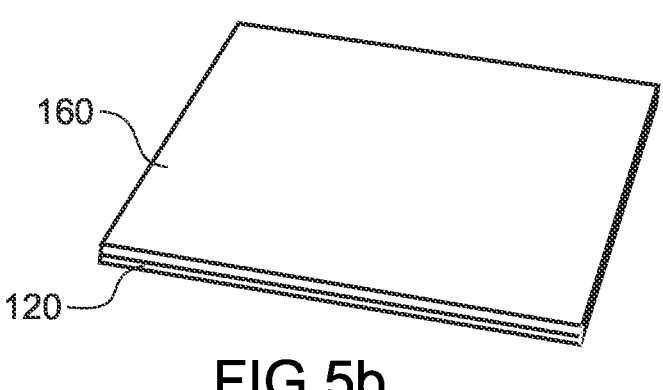

As shown in FIG. 5b, the second layer 160, made in particular of silicon nitride, is formed over the first layer 120.

Figure 5C:
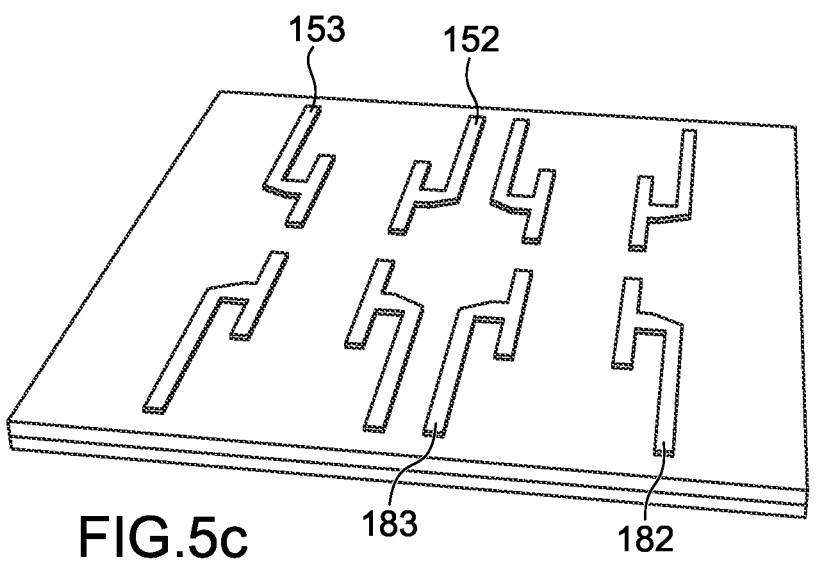

FIG. 5c is a representation of a step for forming the contacts, and in particular the source and drain electrodes of the various transistors. This step involves more particularly the formation of a titanium layer and a gold layer, followed by the definition of the pattern relative to said electrodes by a photolithography/etching sequence (in particular by a wet process).

Figure 5D:
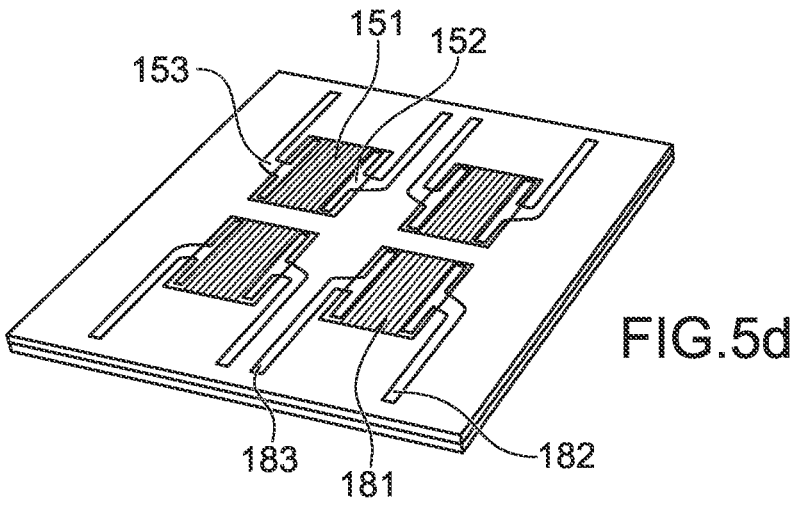

A monolayer of graphene is then transferred onto the second layer 160 using a liquid transfer process (technique referred to as "fishing") and shaped to prevent any crosstalk between the transistors (FIG. 5d).

Figure 5E:
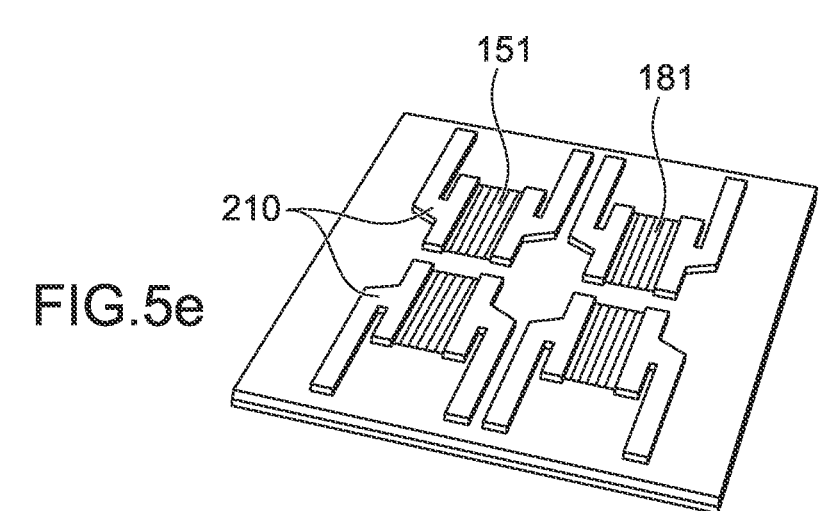

An electrical passivation layer 210 is then formed on the source and drain electrodes to protect them. The electrical passivation layer may involve the use of a SU8 type resin (FIG. 5e).

Figure 5F:
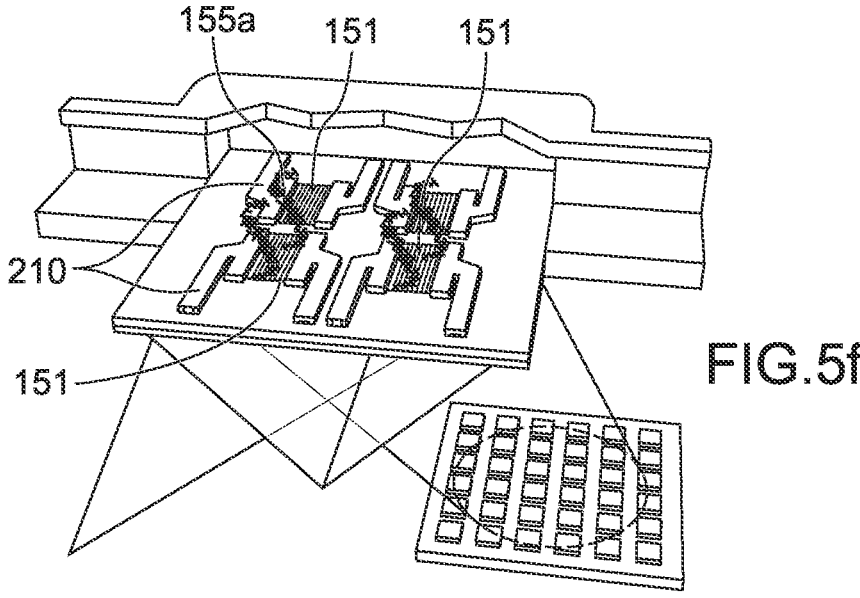

A last step, shown in FIG. 5f, of biological functionalisation may be performed.

REFERENCES

[1] Milan N. Stojanivic et al., "Aptamer-Based Folding Fluorescent Sensor for Cocaine", J. Am. Chem. Soc., 123, 4928-4931, 2001;

[2] Lisa R. Paborsky et al., "The Single-stranded DNA Aptamer-binding Site of Human Thrombin", The Journal of Biological Chemistry, 28(5), 20808-20811, 1993.

The invention claimed is:

1. A biological and/or biochemical and/or chemical sensor, comprising:

a prism;

a first metal layer comprising a contact face covering a first face of the prism;

a light source configured to emit light radiation at an angle of incidence $\theta i$ on the contact face;

a detector configured to collect the light radiation emitted by the light source and reflected by the contact face;

a second layer comprising dielectric material covering the first metal layer; and a transistor resting on the second layer, wherein the transistor comprises a channel region provided in a first sheet comprising a two-dimensional material, wherein the first sheet has a rear face resting on the second layer, and a front face, opposite the rear face, wherein the front face of the first sheet comprises a functionalization comprising specific probes suitable for absorbing one or more specific targets of a target family, and wherein the functionalization is configured to place adsorbed specific targets at a distance lower than a detection distance Dd, below which combined detection by electrical measurement with the transistor and by surface plasmon resonance measurement is possible.

2. The sensor of claim 1, wherein the functionalization is further configured to maintain any target, other than the specific target and susceptible to adsorption at the specific probes, at a distance greater than the detection distance Dd, such that only the detection of targets by surface plasmon resonance is possible.

3. The sensor of claim 1, wherein the specific probes are biological or biochemical or chemical agents grafted onto the front face, wherein each specific probe is configured so that when the specific target is adsorbed at the specific probe, the specific probe deforms in order to place the specific target at a distance from the front face lower than the detection distance Dd.

4. The sensor of claim 1, further comprising:

a reference transistor comprising a second channel region provided in a reference sheet comprising two-dimensional material, wherein the reference sheet has a second rear face resting on the second layer, wherein the reference sheet further comprises a reference face configured to non-selectively absorb general targets, so that the general targets can be detected in a combined measurement, at a level of the reference face, by resonance of surface plasmons initiated by the light source, and by electrical measurement with the reference transistor.

5. The sensor of claim 1, further comprising:

a site, at a section exposed to an external environment of the first metal layer, dedicated solely to surface plasmon resonance measurement.

6. The sensor of claim 1, wherein the two-dimensional material comprises graphene.

7. The sensor of claim 1, wherein the first metal layer comprises gold, or aluminum, or copper, or silver.

8. The sensor of claim 1, further comprising:

a cover covering with the first face, wherein a fluid, flowing from an inlet path to an outlet path of the cover is capable of molecular recognition by the sensor.

9. The sensor of claim 1, wherein the light source and the detector are arranged to enable measurements at different angles of incidence $\theta i$.

10. The sensor of claim 1, wherein the light source is polychromatic, and wherein the light source is arranged with respect to the detector so that a surface plasmon reference measurement is performed at a fixed angle.

11. The sensor of claim 1, wherein the detector is a matrix detector.

12. The sensor of claim 1, wherein the functionalization promotes the adsorption of targets of the *Escherichia coli* family of bacteria, and recognition of a target specific to the *Escherichia coli* family.

13. The sensor of claim 1, wherein the functionalization promotes the adsorption of targets of the cocaine family.

14. The sensor of claim 1, wherein the functionalization promotes the adsorption of $\alpha$-thrombin.

15. The sensor of claim 1, wherein the first metal layer forms a gate electrode of the reference transistor.

16. The sensor of claim 1, wherein the two-dimensional material comprises molybdenum sulfide.

17. The sensor of claim 1, wherein the two-dimensional material comprises graphene and molybdenum sulfide.

18. The sensor of claim 1, wherein the first metal layer comprises gold and silver.

19. The sensor of claim 1, wherein the light source and the detector are arranged to enable measurements at different angles of incidence $\theta i$, wherein the light source is polychromatic, and wherein the light source is arranged with respect to the detector so that a surface plasmon reference measurement is performed at a fixed angle.

20. The sensor of claim 1, wherein the light source and the detector are arranged to enable measurements at different angles of incidence $\theta i$, wherein the light source is polychromatic, wherein the light source is arranged with respect to the detector so that a surface plasmon reference measurement is performed at a fixed angle, and wherein the detector is a matrix detector.

* * * * *